US006921537B2

(12) United States Patent
Zlotnick

(10) Patent No.: US 6,921,537 B2
(45) Date of Patent: Jul. 26, 2005

(54) PREPARATION AND USES OF LOS-DEPLETED OUTER MEMBRANE PROTEINS OF GRAM-NEGATIVE COCCI

(75) Inventor: Gary W. Zlotnick, Penfield, NY (US)

(73) Assignee: Wyeth, Madison, NJ (US)

(*) Notice: Subject to any disclaimer, the term of this patent is extended or adjusted under 35 U.S.C. 154(b) by 515 days.

(21) Appl. No.: 10/091,233

(22) Filed: Mar. 5, 2002

(65) Prior Publication Data

US 2002/0136741 A1 Sep. 26, 2002

Related U.S. Application Data

(60) Division of application No. 08/469,842, filed on Jun. 6, 1995, now Pat. No. 6,355,253, which is a continuation-in-part of application No. 08/061,581, filed on May 13, 1993, now abandoned.

(51) Int. Cl.[7] ...................... A61K 39/02; A61K 39/095; A61K 39/102

(52) U.S. Cl. ................ 424/234.1; 424/250.1; 424/251.1; 424/256.1; 424/279.1; 530/300; 530/350; 530/361; 530/412

(58) Field of Search .......................... 424/234.1, 250.1, 424/251.1, 256.1, 279.1; 530/300, 350, 361, 412

(56) References Cited

U.S. PATENT DOCUMENTS

| | | | |
|---|---|---|---|
| 4,271,147 A | 6/1981 | Helting et al. | 424/92 |
| 4,386,066 A | 5/1983 | O'Rourke et al. | 424/92 |
| 4,601,903 A | 7/1986 | Frasch | 424/92 |
| 4,707,543 A | 11/1987 | Zollinger et al. | 530/402 |
| 5,601,831 A | 2/1997 | Green et al. | 424/256.1 |

FOREIGN PATENT DOCUMENTS

| | | |
|---|---|---|
| DE | 3516017 A1 | 11/1986 |
| EP | 0 073 169 | 3/1983 |
| EP | 0 090 660 | 10/1983 |
| EP | 0 182 401 | 5/1986 |
| EP | 0 301 992 | 2/1989 |
| EP | 0 351 604 | 1/1990 |
| WO | WO 90/06696 | 6/1990 |
| WO | WO 90/10458 | 9/1990 |
| WO | 90/13032 | 11/1990 |
| WO | WO 93/03761 | 3/1993 |

OTHER PUBLICATIONS

Beuvery, E.C. et al., "Preparation and Physicochemical and Immunological Characterization of Polysaccharide–Outer Membrane Protein Complexes of *Neisseria meningitidis*," *Infection and Immunity*, 40(1):369–380 (1983).

Wedege, E. et al., "Restoration of Antibody Binding to Blotted Meningococcal Outer Membrane Proteins Using Various Detergents," *J. Immunol. Methods*, 113:51–59 (1988).

Zlotnick, G.W. et al., "Purification and Characterization of a Peptidoglycan–Associated Lipoprotein from *Haemophilus influenzae*," *J. Biol. Chem.*, 263(20):9790–9794 (1988).

Poolman, J.T. et al., "Comparison of Meningococcal Outer Membrane Protein Vaccines Solubilized with Detergent or C Polysaccharide," *Antonie van Leeuwenhoek J. of Microbiology*, 53(6):413–419 (1987).

Kittel, J., "Isolation of Proteins from Biological Membranes by Solubilisation With Limited Amount of Detergent," (1994) *Derwent Info. Ltd.* (WPI Acc No.: C86–138270) (Abstract : DE 3516017).

Helenius, A. and Simons, K., "Solubilization of Membranes by Detergents," *Biochimica et Biophysica Acta*, 415:29–79 (1975).

Moriyon, I. and Berman, D.T., "Effects of Nonionic, Ionic, and Dipolar Ionic Detergents and EDTA on the *Brucella* Cell Envelope," *J. Bacteriology*, 152(2):822–828 (1982).

Murphy, T.F. and Bartos, L.C., "Surface–Exposed and Antigenically Conserved Determinants of Outer Membrane Proteins of *Branhamella catarrhalis*," *Infection and Immunity*, 57(10):2938–2941 (1989).

"Other Species of Neisseria and Related Genera" In *Davis Microbiology*, 3rd; Gotschlich, E.C., ed., The Niesseriae, Chapter 30, pp. 643–644.

Mandrell, R.E. and Zollinger, W.D. "Human Immune Response to Meningococcal Outer Membrane Protein Epitopes after Natural Infection or Vaccination," *Infect. Immun.*, 57:1590–1598 (1989).

Frasch, C.E. and Peppler, M.S., "Protection Against Group B *Neisseria meningitidis* Disease: Preparation of Soluble Protein and Protein–Polysaccharide Immunogens," *Infection and Immunity*, 37(1):271–280 (1982).

"Centocor Stops Trials of Flagship Drug," *The Washington Post*, p. D3, Jan. 19, 1993.

Spalding, B.J., "In Shocking Synergen, Sepsis Tallies Third Victim," *Bio/Technology*, 11:428–429 (1993).

Peppler, M.S. and Frasch, C.E., "Protection Against Group B *Neisseria meningitidis* Disease, Effect of Serogroup B Polysaccharide and Polymyxin B Immunogenicity of Serotype Protein Preparations," *Infection and Immunity*, 37:264–270 (1982).

Collins, M.L.P. and Salton, M.R.J., "Preparation and Crossed Immunoelectrophoretic Analysis of Cytoplasmic and Outer Membrane Fractions from *Neisseria gonorrhoeae*," *Infection and Immunity*, 30(1):281–288 (1980).

(Continued)

Primary Examiner—Rodney P Swartz
(74) Attorney, Agent, or Firm—Hamilton, Brook, Smith & Reynolds, P.C.

(57) ABSTRACT

Described herein is a method for removing toxic lipooligosaccharide (LOS) from outer membranes of Gram-negative cocci, such as *Neisseria meningitidis*. LOS-depleted outer membranes and LOS-depleted soluble outer membrane proteins can be prepared, which are able to elicit bactericidal antibodies against homologous strains of bacteria. Vaccines and other uses of the preparations are further described.

29 Claims, 2 Drawing Sheets-

OTHER PUBLICATIONS

Mandrell, R.E. and Zollinger, W.D., "Use of a Zwitterionic Detergent for the Restoration of the Antibody–Binding Capacity of Electroblotted Meningococcal Outer Membrane Proteins," *J. Immunol. Methods*, 67:1–11 (1984).

Catlin, B.W., "Branhamaceae New Family a Proposed Family to Accommodate the Genera Branhamella and Moraxella," *Int'l. J. Systematic Bact.*, 41(2):320–323 (1991) (Abstract only).

Saukkonen, K. et al., "Protective Efficacy of Monoclonal Antibodies to Class 1 and Class 3 Outer Membrane Proteins of *Neisseria meningitidis* B:15:P1.16 in Infant Rat Infection Model: New Prospects for Vaccine Development," *Microbial Pathogenesis*, 3:261–267 (1987).

Schnaitman, C.A., "Effect of Ethylenediaminetetraacetic Acid, Triton X–100, and Lysozyme on the Morphology and Chemical Composition of Isolated Cell Walls of *Escherichia coli*," *J. Bacteriology*, 108(1):553–563 (1971).

Frasch, C.E. and Gotschlich, E.C., "An Outer Membrane Protein of *Neisseria meningitidis* Group B Responsible for Serotype Specificity," *J. Exper. Medicine*, 140:87–104 (1974).

Campagnari, A.A., et al., "Lipooligosaccharide Epitope Shared Among Gram–Negative Non–Enteric Mucosal Pathogens," *Microb Pathology*, 8:353–362 (1990).

Smyth, C.J., et al., "Immunology of Outer Membrane Proteins of Gram–Negative Bacteria", *Immunology of the Bacterial Cell Envelope*, Chapter 7: 177–201 (1995).

Frasch, C.E., et al., "New Developments in Meningococcal Vaccines", *Meningococcal Protein Vaccines*, 633–639 (1985).

Preparation of LOS-Depleted *Neissėria meningitidis* Outer Membrane Proteins

2996 CELLS lyophilized resuspended in hypotonic buffer lyse in French press

CELL LYSATE salt wash ultracentrifugation

CELL ENVELOPES (TOTAL MEMBRANES)

1% TRITON X-100™ extraction (at least 2X)

ultracentrifugation

OUTER MEMBRANES

1% ZWITTERGENT 3-14™ extraction (at least 2X)

LOS-DEPLETED OUTER MEMBRANES

1% ZWITTERGENT 3-14™ + 0.5 M NaCl extraction

LOS-DEPLETED SOLUBLE OUTER MEMBRANE PROTEINS

80% ethanol extraction

CONCENTRATED SOLUBLE OUTER MEMBRANE PROTEINS

PREPARATION AND USES OF LOS-DEPLETED OUTER MEMBRANE PROTEINS OF GRAM-NEGATIVE COCCI

RELATED APPLICATIONS

This application is a divisional of U.S. patent application Ser. No. 08/469,842, filed Jun. 6, 1995, now U.S. Pat. No. 6,355,253, issued Mar. 12, 2002, which is a continuation-in-part of U.S. patent application Ser. No. 08/061,581, filed May 13, 1993, now abandoned. The entire teachings of the above applications are incorporated herein by reference.

BACKGROUND

Bacterial meningitis is an inflammatory disease of the central nervous system caused by the growth of bacteria in and adjacent to the leptomeninges. It is an acute, and often lethal, infectious disease that affects children and young adults. One of the most common causes of bacterial meningitis worldwide is infection with *Neisseria meningitidis*. The occurrence of infection with this bacterium is unpredictable, since many people become colonized without exhibiting the disease. Some people are temporary carriers, while others are chronic carriers, discharging meningococci either more or less continuously or in a sporadic fashion. During the course of infection, bactericidal antibodies are produced in the infected person, which apparently immunize the person against subsequent infection (Goldschneider, I., et al., *J Exp. Med.* 129:1327–1348 (1969)). This observation has led to the expectation that vaccines based on bacterial antigens may be effective against meningitis.

*N. meningitidis* is a Gram-negative coccus. Characteristically, it is surrounded by a cell envelope composed of an inner plasma membrane, a periplasmic space, and an outer membrane or cell wall. The outer membrane is composed of lipooligosaccharide (LOS) molecules, lipids, proteins and polysaccharides. The protective antibodies produced in infected people were found to be directed against both the capsular polysaccharides and the outer membrane proteins (Frasch, C. E., *In Medical Microbiology* (eds. C. S. F. Easman and J. Jeljaszewicz), Academic Press, New York, Vol. 2, pp. 115–144 (1983)).

Strains of *N. meningitidis* have been classified into serogroups according to the type (antigenically and biochemically) of the capsule. Currently recognized serogroups include A, B, C, D, W135, X, Y, Z and 29E. The polysaccharides responsible for the serogroup specificity of groups A, B, C, X, W135 and Y have been purified. A tetravalent vaccine based on purified capsular polysaccharides from serogroups A, C, Y and W 135 has been developed (Hankins, W. A., et al., *Proc. Soc. Exp. Biol. Med.* 169:54–57 (1982)). However, the lack of immunogenicity in the under 2 years age group, the age group most at risk from meningococcal infection, has limited the usefulness of this vaccine. The capsule of Group B *N. meningitidis* is poorly immunogenic in all age groups, even when conjugated to a carrier protein. There is evidence that antibodies to this capsule may cross react with brain tissue of fetal and newborn infants.

The major outer membrane proteins (omp) of *N. meningitidis* have been divided into five classes on the basis of structural similarities, as determined by migration (Mr) on SDS-polyacrylamide gels and peptide map analysis (Tsai, C. M., et al., *J Bacteriol.* 146:69–78 (1981)). Of these protein classes, the class 1 protein appears to be the most interesting for vaccine production. This antigen seems to be a major immunodeterminant in humans. It is expressed in most isolates of *N. meningitidis* and is the basis for subtype specificity of strains.

Several attempts have been made to produce a vaccine based on outer membrane proteins. Vaccines composed of capsular polysaccharide and outer membrane proteins, or just outer membrane proteins in a vesicular complex, have been tested. Only one of these vaccines has been reported to be more than 57% effective (Sierra, G. V. G., et al., *NIPH Annals* 14(2):195–210 (1991)).

Another significant problem in the development of both outer membrane and capsule based vaccines is the presence of the bacterial lipooligosaccharide (LOS), which produces toxic side effects in humans. LOS is also referred to as bacterial endotoxin. Low amounts of LOS can cause fevers, and high doses of LOS can result in a general wasting (cachexis) of the patient. The most recent outer membrane complex vaccines have had residual LOS levels of 10–70 $\mu$g/mg protein (see Zollinger, W. D., In *New Generation Vaccines* (eds. G. C. Woodrow and M. M. Levine), Marcel Dekker, Inc., New York, pp. 325–348 (1990)). Thus, there exists a need for safe and effective vaccines for bacterial meningitis caused by *N. meningitidis*, and especially for disease caused by Group B strains.

SUMMARY OF THE INVENTION

This invention relates to a method for the effective removal of lipooligosaccharide (LOS) from outer membranes of Gram-negative cocci by sequential extractions with certain detergents. LOS, which is also referred to as bacterial endotoxin, can cause undesirable side effects in vaccines, such as fever. As described herein, the method produces outer membranes and soluble outer membrane proteins with an extremely low content of LOS, but which retain immunogenicity. These LOS-depleted outer membrane products are further shown to elicit bactericidal antibodies which confer protection against *Neisseria meningitidis* in animals. Thus, vaccines comprising LOS-depleted outer membranes and soluble outer membrane proteins are provided, which are expected to be useful in therapy and prophylaxis against meningitis and other diseases caused by Gram-negative cocci.

Specifically described herein are outer membrane products of *Neisseria meningitidis*. Outer membrane products prepared from *N. meningitidis* by the present method are shown to have a LOS content of less than about 0.01% (wt./wt. total protein) and to elicit antibodies which are both bactericidal and protective in animals. As a result, vaccines against neisserial meningitis are provided, which are immunogenically effective and relatively free of bacterial LOS. Of particular interest is a vaccine against serogroup B strains of *N. meningitidis*, for which there is presently no effective vaccine.

The present method is expected to also be applicable to other Gram-negative cocci, since these bacteria have structurally similar outer membranes. For example, LOS-depleted outer membranes of other *Neisseria* species, such as *N. gonorrhoeae*, and other Gram-negative cocci, such as *Moraxella*, can be prepared. Thus, *N. meningitidis* is representative of other Gram-negative cocci in the procedures and products described below.

This method is further applicable to various natural strains of Gram-negative cocci, as well as to recombinant strains that are genetically engineered to produce more than one subtype-specific epitope, e.g., more than one class 1 protein of *N. meningitidis*. Multivalent vaccines can be prepared using mixtures of strains or recombinant strains expressing the surface epitopes of several serogroups, serotypes or subtypes.

The method comprises sequential extractions with different kinds of detergents. First, total membranes of the cocci are extracted with a polyoxyethylene detergent (e.g., TRITON X-100™, BRIJ35™, or TWEEN80™), resulting in outer membranes that are depleted of inner membranes and some of the LOS. This is followed by extraction of the outer membranes with a zwitterionic betaine detergent, such as one of the ZWITTERGENT™ series (e.g., 3-12 or 3-14) or EMPIGEN BB™. These detergents specifically remove essentially all of the remaining LOS while extracting very little protein.

The resulting LOS-depleted outer membrane preparation is composed of outer membrane proteins (omps) complexed with cell wall components. This preparation can be used for vaccine purposes directly, or the omp can be solubilized and extracted from the other cell wall components using a zwitterionic betaine detergent in a salt buffer, e.g., with ZWITTERGENT 3-14™ in about 0.1 to about 0.5 M NaCl. The solubilization step results in LOS-depleted fractions, one containing soluble outer membrane proteins and another containing insoluble outer membrane proteins complexed with other cell wall components. Both LOS-depleted outer membranes and LOS-depleted soluble outer membrane proteins are shown to elicit bactericidal antibodies in mice.

BRIEF DESCRIPTION OF THE DRAWINGS

FIG. 1 is a flow diagram of a method for preparing LOS-depleted soluble outer membrane proteins from *N. meningitidis*.

DETAILED DESCRIPTION OF THE INVENTION

Figure 2:
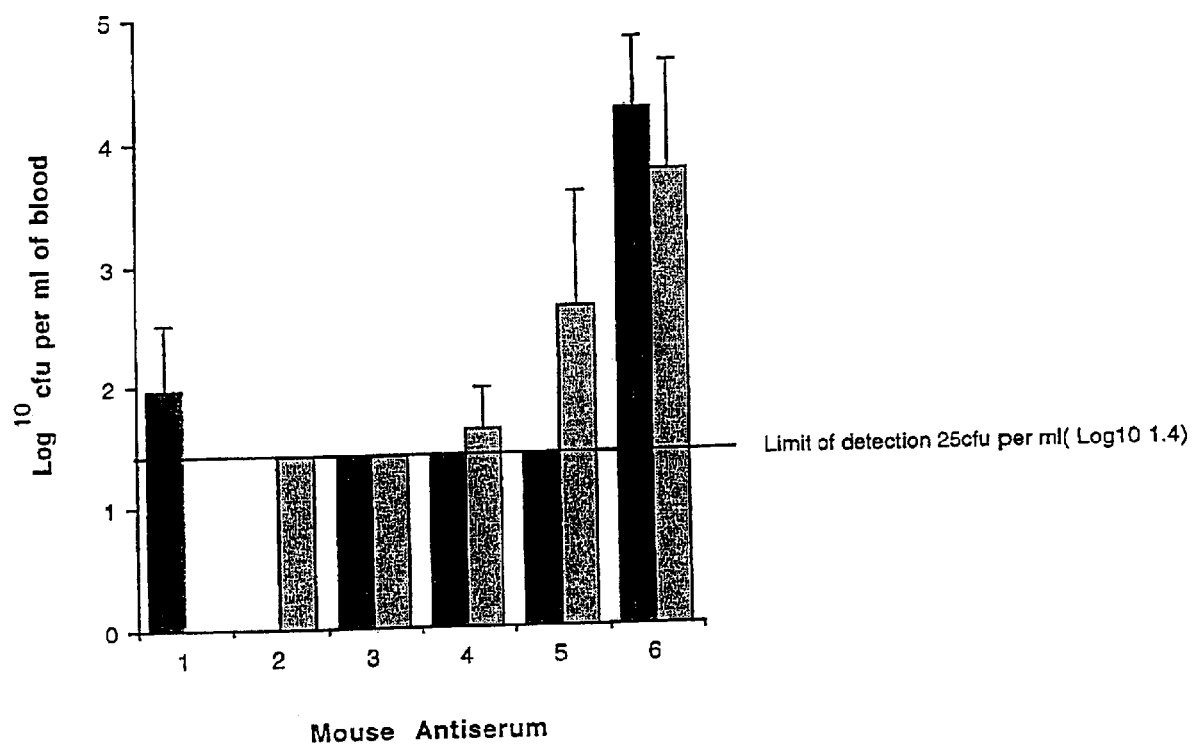
FIG. 2 is a bar graph illustrating the protective effect of LOS-depleted soluble outer membrane proteins (SOMP-LOS) from *N. meningitidis* against challenge in infant rats with H44/76 and/or 2996 cells. Darkly shaded bars indicate infant rats challenged with H44/76; lightly shaded bars indicate infant rats challenged with 2996. Antiserum used is shown across the bottom of the graph as follows: column 1, (SOMP-LOS) from H44/76 (1:5 dilution); column 2, SOMP-LOS from 2996 (1:5 dilution); column 3, 2996/H44/76 mixture (1:5 dilution); column 4, 2996/H44/76 mixture (1:10 dilution); column 5, 2996/H44/76 mixture (1:20 dilution); and column 6, pool of week 0 (1:5 dilution).

An effective method is described herein for removing the toxic lipooligosaccharides (LOS) from outer membrane preparations of Gram-negative cocci, as exemplified by *Neisseria meningitidis*. The method is simple and results in a lower content of LOS than achieved with previous methods for detoxifying outer membrane preparations. In addition, LOS is removed without significant loss of immunogenicity.

The method involves sequential extractions with different types of detergents. First, total membranes of the cocci are extracted with a polyoxyethylene detergent, such as TRITON X-100™, BRIJ35™or TWEEN80™. This removes the inner membranes and some of the LOS. Then, the outer membranes are extracted with a zwitterionic betaine detergent, such as one of the ZWITTERGENT™ series (e.g., 3-12 or 3-14) or EMPIGEN BB™. This step removes essentially all of the remaining LOS, resulting in LOS-depleted, protein-enriched outer membrane complexes (referred to as LOS-depleted outer membranes). Trace amounts of LOS may remain, depending on the particular zwitterionic detergent used; however, these levels are low and are not expected to induce toxic side effects in humans.

The preferred procedure is to extract several times with TRITON X-100™ followed by several extractions with ZWITTERGENT 3-14™ (Zw3-14). For example, LOS-depleted outer membranes are prepared from a serogroup B strain, such as H44/76, 2996 or H13. Bacterial membranes are extracted twice with TRITON X-100™, then at least twice with ZWITTERGENT 3-14™ (see FIG. 1). The resulting yield from one gram of lyophilized bacterial cells is approximately 32 mg of LOS-depleted, protein-enriched outer membranes. This product contains no remaining LOS detectable by silver staining of SDS-polyacrylamide gels.

The LOS-depleted outer membrane product of this method is a complex of outer membrane proteins and cell wall components. To further purify the antigen preparation, the outer membrane proteins (omps) are solubilized from the LOS-depleted cell walls, preferably, by extraction with a zwitterionic betaine detergent in a salt buffer. ZWITTERGENT 3-14™ in about 0.1 to about 0.5 M sodium chloride is preferred for this purpose. Other zwitterionic detergents and salt buffers, such as potassium chloride, can also be used. The solubilization step yields LOS-depleted soluble outer membrane proteins and a separate fraction containing insoluble omps complexed with other cell wall components. A yield of approximately 16 mg solubilized omps per gram of lyophilized cells is obtained by extracting LOS-depleted cell walls with 1.0% ZWITTERGENT 3-14™ in 0.5 M sodium chloride. More protein can be obtained by repeating this extraction step.

The soluble outer membrane proteins are further concentrated by various standard methods for protein concentration, such as ethanol precipitation, filtration, and absorption. Concentration of the soluble omps permits adjusting the final concentration of the antigens in a vaccine or reagent composition.

FIG. 1 illustrates one embodiment of the method for preparing LOS-depleted soluble outer membrane proteins, beginning with whole *N. meningitidis* cells and proceeding to concentration of the soluble outer membrane proteins. Table 1 (at the end of the Detailed Description) shows the LOS and protein contents of the LOS-depleted outer membranes and soluble omps compared with the starting material.

The types of detergent used and the order in which they are used are important to this method. For example, TRITON X-100™ efficiently removes the majority of the LOS from the outer membranes with minimal loss of protein. However, it is ZWITTERGENT 3-14™ that is important for removal of the remainder of the LOS. The order of detergents used is important in determining whether a protein or other cell wall component is extracted or left insoluble. Each detergent has a direct effect on what is solubilized with subsequent detergents. For example, if sarcosyl, instead of TRITON X-100™, is used to extract inner membranes, the protein profile of the resulting outer membranes, as determined by SDS-polyacrylamide gel electrophoresis, is different. The level of class 1 outer membrane protein is also reduced.

Various optimizations of the method described above can be performed in order to maximize LOS removal and minimize protein loss. For example, it is found that the optimum concentration range of Zw3-14 is from about 0.5% to about 1.0% (wt./vol.). Levels lower than 0.5% are not effective at decreasing the endotoxin level. Each extraction step can also be performed more than once. However, extraction with the polyoxyethylene detergents should precede extraction with the zwitterionic detergents. Extracting a number of times may result in cleaner preparations, but may also result in lower yields. Increasing the concentration of detergents may produce the same result with fewer extractions. Combinations of different polyoxyethylene detergents and zwitterionic detergents can also be used in the first and second extraction steps, respectively. For example, after TRITON™ extraction, the outer membranes can be extracted twice with Zw3-12 and twice with Zw3-14.

Total membranes are prepared from the cocci by standard methods for lysing bacterial cells and separating the membrane and cytoplasmic fractions. For example, a French pressure cell is utilized to lyse the bacteria, low speed centrifugation to remove unbroken cells, and ultracentrifugation to recover total membranes. Separation of the desired from the undesired fractions after each extraction can also be performed by a variety of known methods, including centrifugation, filtration, dialysis, and absorption.

Detergent Substitutions

Various detergent substitutions can be used in the method and their effectiveness at removing LOS while retaining immunogenicity of the outer membranes tested.

BRIJ™, TRITON X-100™, and TWEEN80™ are polyoxyethylene detergents. BRIJ35™ and TWEEN80™ perform very similarly to TRITON™. Neither reduces the endotoxin level as effectively as TRITON X-100™, but they do not affect the subsequent removal of LOS by ZWITTERGENT 3-14™. Total protein content of the resulting LOS-depleted outer membrane products are similar. Substitution of TRITON X-100™ with sarcosyl results in low endotoxin content (much less than 1.8 ng/mg protein), but the yield of LOS-depleted outer membranes in terms of total protein is much lower than obtained with TRITON™.

The zwitterionic betaine detergents are summarized by the following formula:

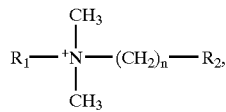

where $R_1$ is an alkyl chain with more than 10 carbons and less than or equal to 16 carbons, $R_2$ is a sulfonyl group or a carboxyl group, and n is greater than 1 and preferably 2–3. For example, the ZWITTERGENT™ series has $R_2$=a sulfonyl group ($-SO_3^{31}$), n=3, and $R_1$ alkyl groups of various lengths. The ZWITTERGENT™'s are named after the length of the alkyl chain, e.g., Zw3-12 has an alkyl group with 12 carbons, and Zw3-14 has 14 carbons in $R_1$. EMPIGEN BB™ has $R_2$=a carboxyl group ($-COO^-$), 12 carbons in $R_1$, and n=2.

Of ZWITTERGENTS™ 3-08, 3-10, 3-12 and 3-14, 3-14 is the most effective at removing endotoxin without extracting an excess of protein. The shorter chain detergents (3-08 and 3-10) are significantly less effective at removing LOS and also yield less protein. These results suggest that the chain length of the $R_1$ alkyl group affects the effectiveness of the detergent at removing LOS. It is possible that Zw3-12 and Zw3-14 are effective because their alkyl chains are about the same length as the aliphatic chains of the LOS molecules. However, detergents with alkyl groups longer than 16 carbons may become insoluble.

EMPIGEN BB™ functions substantially identically to Zw3-14. It is as effective at reducing the level of endotoxin and extracts the same proteins. It may offer an advantage in that it seems to extract less protein, resulting in increased total protein in the outer membrane products.

Other detergents that are similar in structure to the ones specifically mentioned herein can be tested for effectiveness in preparing LOS-depleted outer membranes and outer membrane proteins, as described herein. Such detergents would be considered the functional equivalents of the polyoxyethylene detergents in the first extraction step or of the zwitterionic detergent used in the second extraction step or in the solubilization step.

Immunogenicity of Outer Membrane Products

To test the immunogenicity of the outer membrane products of this method, outer membranes (the product after extraction with TRITON X-100™), LOS-depleted outer membranes (the product after extraction with Zw3-14, or Zw3-12 as indicated), and LOS-depleted soluble omps (the product of the solubilization step) are prepared from a recombinant strain (H13) of N. meningitidis. Strain H13 (B:-:p1.7,16;p1.5,2) is a double mutant cell line derived from the wild type strain H44/76 (B:15:p1.7,16). H13 is devoid of the class 3 and is genetically engineered to express the p1.5,2 class 1 protein in addition to its natural p1.7,16 class 1 protein. The wild type strain 2996 (B:2B:p1.5,2) expresses the p1.5,2 class 1 protein. Thus, H13 has the class 1 subtypes of both H44/76 and 2996.

The LOS-depleted outer membrane preparations are tested for immunogenicity by injecting them into mice and analyzing the resulting sera. The sera are collected at 0, 4, and 8 weeks after primary immunization and at exsanguination on week 10 (see Examples). The sera are then tested, by immunoblot analysis and enzyme-linked immunosorbent assay (ELISA), for the presence of antibodies that react with whole cells from strains H44/76 or 2996, as well as for antibodies that recognize purified p1.7,16 class 1 omp.

Table 2 shows the endpoint ELISA titers of the sera to purified p1.7,16. As seen in this table, the LOS-depleted soluble omps (SOMP-LOS) elicit the highest antibody titers against purified p1.7,16, while the titers of sera elicited by outer membranes and LOS-depleted outer membranes (OM-LOS) are lower but approximately equal. Western immunoblot analysis with the sera against outer membranes from both H44/76 and 2996 cells and purified p1.7,16 indicates that the sera contain only antibodies against outer membrane proteins and not antibodies against LOS.

Tables 3 and 4 show the endpoint ELISA titers of the sera to H44/76 and 2996 whole cells, respectively. The titers of sera from LOS-depleted outer membranes prepared using Zw3-12, as well as Zw3-14, are shown. The ELISA titers of all three antisera are similar against H44/76 whole cells (Table 3). The serum elicited by the soluble omps and the serum elicited by the LOS-depleted outer membranes appear to approach a plateau stage at exsanguination. The level of antibodies in sera elicited by crude outer membranes appears to increase linearly. In ELISAs against 2996 whole cells (Table 4), the titers of sera elicited by crude outer membranes and those elicited by LOS-depleted outer membranes are approximately equal, and both are lower than the titer of sera elicited by LOS-depleted soluble omps. These results show that the LOS-depleted outer membrane and soluble omp products of this process are extremely low in endotoxin content without significant loss of immunogenicity. In addition, these results show that antibodies against two strains with different serotypes and subtypes (H44/76 and 2996) are elicited by outer membrane products made from a recombinant strain (H13) that expresses the class 1 subtypes of both strains.

Bactericidal Activity

The ability of the LOS-depleted outer membrane and soluble omp preparations to elicit functional antibodies (i.e. antibodies able to induce complement-mediated destruction of meningococcal cells) is tested by determining the bactericidal activity of the sera. The assay for bactericidal activity is described in the Examples. Table 5 shows the results obtained using outer membranes prepared from strain 2996 (subtype p1.5,2) or the recombinant strain H13 (subtypes p1.5,2 and p1.7,16). LOS-depleted outer membranes and soluble outer membrane proteins of 2996 produce antibodies capable of killing a homologous strain of N. meningitidis, but not a heterologous strain, H44/76. The LOS-depleted outer membrane preparations made from H13, which expresses the class 1 subtypes of both H44/76 and 2996, elicit bactericidal antibodies against H44/76 whole cells, but not against 2996 whole cells. This lack of bactericidal activity against 2996 is not due to loss during the removal of LOS, however, since the crude outer membranes also do not elicit functional antibodies. As shown above, LOS-depleted outer membrane products made from H13 do elicit antibodies against 2996 cells (Table 4). It is possible that the lack of bactericidal activity against 2996 cells under these conditions is due to weak expression of the p1.5,2 class 1 protein in the H13 strain. This is consistent with observations from Western blots that the H13 strain expresses significantly less p1.5,2 protein than the native p1.7,16 class 1 protein. This problem can be overcome by preparing the LOS-depleted outer membranes from a recombinant strain that expresses the recombinant class 1 protein at a level comparable to that of the native class 1 protein. Clones of H13 with stronger expression of p1.5,2 can also be selected by screening filters containing H13 colonies for reactivity to anti-p1.5,2 antibodies. Alternatively, bactericidal antibodies may be elicited by increasing the immunization dose of LOS-depleted outer membranes or soluble omps.

Protection Against N. meningitidis

The ability of the LOS-depleted soluble outer membrane proteins from H44/76 or 2996 cells or both to confer protection against bacteriemia as a result of intraperitoneal challenge with H44/76 or 2996 cells was tested using an infant rat challenge model. The protection assay is described in the Examples, and the results are summarized in FIG. 2.

Sera was obtained from Swiss Webster mice vaccinated (with LOS-depleted soluble outer membrane proteins from H44/76 or 2996 cells or both) and bled at weeks 0 and 4. Immunogenicity of the sera was determined as described in the Examples, and the results are summarized in Table 6. This antisera was used to protect infant rats as described in the Examples; infant rats were vaccinated with either H44/76 (FIG. 2, column 1), 2996 (column 2), or a 2996/H44/76 mixture at dilutions of 1:5, 1:10 or 1:20 (columns 3, 4 and 5, respectively). Sera collected at week 0 was used as a control (column 6). The infant rats were then challenged intraperitoneally with either H44/76 or 2996 cells, and the number of colony forming units per milliliter of blood was recorded.

FIG. 2 shows a significant decline in the number of bacterial colony forming units in the vaccinated rats as compared with the control (compare bars 6 with bars 1-5). This data indicates that the antibodies elicited by the LOS-depleted soluble outer membrane protein vaccines confer protection against the homologous strain of N. meningitidis in the infant rat challenge model. Furthermore, a mixture of the H44/76 and 2996 LOS-depleted soluble outer membrane proteins, when adjuvanted with QS-21, elicits antibodies that bind to the surface of both strains and are both functional and protective in the infant rat assay.

Utility of the Invention

The method described above is useful for preparing vaccines against N. meningitidis and other Gram-negative cocci. Methods of therapy or prophylaxis against diseases (e.g. meningitis) caused by these cocci are thus provided. Previous methods of vaccine preparation follow a strategy of first extracting the outer membrane proteins (omp) from cell walls and then removing as much LOS as possible. The present method differs from previous methods in that it removes the LOS prior to extraction of the outer membrane proteins. As a result, the LOS content is greatly reduced without significant loss of immunogenicity from outer membrane proteins.

The present method can remove LOS to as little as less than 0.01% (wt./wt. total protein) prior to solubilization of omp. The soluble omp preparation contains less than about 3.0 ng LOS per µg protein. This is 40× less endotoxin than reported by Zollinger et al. for their vaccine in 1978 (Zollinger, U.S. Pat. No. 4,707,543) and 100× less endotoxin than is currently being tested in Cuba and Brazil (Sierra et al., 1991).

A further advantage is that two types of LOS-depleted preparations are produced, outer membrane complexes and soluble outer membrane proteins, both of which are immunogenic and low in LOS content. A soluble antigen preparation permits greater flexibility in choosing adjuvants and easier administration of the vaccine. It is notable that the preparation of soluble outer membrane proteins is capable of eliciting a functional antibody response in the absence of a vesicular structure. All previous vaccine trials utilize an outer membrane complex or vesicular form (Sierra et al., 1991). In addition, these previous vaccines have low but measurable levels of LOS. In fact, the previous vaccine against serogroup B N. meningitidis contains 1% LOS by weight relative to total protein.

The present method is useful for preparing multivalent vaccines. For example, in one embodiment, LOS-depleted outer membranes or soluble omps are made using a mixture of strains of various serogroups, serotypes and subtypes of N. meningitidis. In another embodiment, recombinant strains that express a mixture of strain-specific outer membrane epitopes, such as various class 1 protein subtypes, are used as starting material for vaccines with broader protective value. The cloning (Barlow, A. K., et al., Infection and Immunity 55(11):2734–2740 (1987)) and sequences of a number of class 1 omps of N. meningitidis and the construction of recombinant bacterial strains have been previously described (Seid, R. C., et al., WO 90/06696, "Meningococcal Class 1 Outer-Membrane Protein Vaccine", Jun. 28, 1990).

The LOS-depleted outer membrane preparations, including the soluble omps, are also useful as diagnostic reagents, for example, to distinguish antibodies against cell walls or omps from antibodies against coccal capsules or LOS. Furthermore, the immunogenic preparations are useful for raising antibodies that recognize omps or cell walls, but not capsular saccharides.

This method of preparing LOS-depleted outer membranes and soluble omps is expected to be effective on various Gram-negative cocci, since these bacteria have structurally similar outer membranes. For example, LOS-depleted outer membrane products and vaccines can be prepared by this method from other Neisseria, such as Neisseria gonorrhoeae, and from other Gram-negative cocci, such as Moraxella and particularly M. catarrhalis.

The following examples specifically illustrate the invention.

EXAMPLES

N. meningitidis Strains

Neisseria meningitidis H44/76 (B:15:p1.7,16), 2996 (B:2B:p1.5,2), and H13 (B:-:p1.7,16;p1.5,2) cells are kindly supplied by J. T. Poolman, Netherlands. H44/76 was deposited on Dec. 11, 1989 in the Central Bureau Voor Schimmelculturen (CBS), Baarn, The Netherlands, under the terms of the Budapest Treaty and is referenced by CBS G35-89. 2996 and H13 are available from the RIVM, The Netherlands. Strain typing is based on the scheme proposed by Frasch (1983).

N. meningitidis strains are grown from frozen stock of GC agar media (Difco Laboratories, Detroit, Mich.) supplemented with dextrose (4 g/L), glutamine (0.1 g/L), cocarboxylase (0.2 mg/L), and ferric nitrate (5 mg/L). Plates are incubated for 6 hours at 35° C. in 5% $CO_2$. After growing for 6 hours, the colonies from one plate are used to inoculate 100 mL of liquid culture media consisting of 0.2% dialyzed yeast extract, L-glutamic acid (1.3 g/L), L-cysteine-HCl (0.02 g/L), sodium phosphate dihydrate, dibasic (10 g/L), potassium chloride (0.09 g/L), ammonium chloride (1.25 g/L), magnesium sulfate heptahydrate (0.6 g/L), dextrose (5 g/L), and ferric nitrate (100 $\mu$M). This liquid culture is grown at 37° C. for 18 hours. An aliquot of the 18 hour culture is diluted to 20–30 Klett units or an optical density of 0.1 at 650 nm, and the culture is grown to late exponential phase. Once the cells reach late exponential phase, they are heat killed, sedimented, frozen, and lyophilized.

Preparation of LOS-Depleted Meningococcal Outer Membranes and Soluble Outer Membrane Proteins TRITON X-100™, BRIJ™, EMPIGEN BB™ and the ZWITTERGENTS™ are available from Calbiochem, San Diego, Calif. TWEEN80™ is available from ICN Nutritional Biochemicals, Cleveland, Ohio.

1.5 grams of lyophilized, heat killed cells are resuspended in 75 milliliters of a hypotonic solution of 10 mM Hepes-NaOH, pH 7.4, 1 mM EDTA and lysed in an SLM/AMINCO French Pressure Cell. Bacteria are pelleted by centrifugation (5 minutes, 8000×g, 10° C.). The cell lysate is washed with 0.5 M sodium chloride, and the cytoplasmic extract is removed by centrifugation (200,000×g, one hour, 10° C.). Inner membranes are solubilized and removed by centrifugation at 400,000×g for one hour at 10° C. following extraction with 1% TRITON X-100™ in 10 mM Hepes-NaOH, pH 7.4, 1 mM magnesium chloride. This extraction is repeated once. Outer membranes are washed by resuspension in 50 mM Tris-HCl, pH 8.0, 5 mM EDTA, and centrifuged (200,000×g, one hour, 10° C.). They are then extracted twice for one hour each with 1% ZWITTERGENT 3-14™ (w/v) in the same buffer and centrifuged at 400,000×g for one hour at 10° C. Outer membrane proteins are solubilized by extracting the protein-containing cell walls with 1% ZWITTERGENT 3-14™ (w/v) and 0.5 M sodium chloride for one hour at room temperature and concentrated by 80% ethanol (v/v) precipitation. The concentrated outer membrane proteins are solubilized in 50 mM Tris-HCl, pH 8.0, 5 mM EDTA, 1% ZWITTERGENT 3-14™, 0.5 M NaCl.

SDS-PAGE and Immunoblotting

Protein profiles and LOS content of outer membrane vesicles (OMV) and solubilized proteins are analyzed in 15% SDS-polyacrylamide gels with the buffer system of Laemmli (Laemmli, U. K., Nature 227:680–685 (1970)) using BIO-RAD's (Richmond, Calif.) Mini Protean II Dual Slab Gel system. Samples are heated for 5 minutes at 100° C. in sample buffer containing 0.1 M Tris-HCl, pH 7.0, 25 mM dithiothreitol, 2% sodium dodecyl sulfate (SDS), then adjusted to 6% sucrose. Gels are run at 150 V for 45–60 minutes and either silver stained by the method of Morrissey (Morrissey, J. H., Anal. Biochem. 117:307–310 (1981)), or the proteins are transferred onto nitrocellulose for immunoblotting as described in Towbin, H., et al., Proc. Natl. Acad. Sci. USA 76:4350–4355 (1979) or Johnson, D. A., et al., Gene Anal. Technol. 1:3–8 (1984). Blots are blocked for 15 minutes at 37° C. in BLOTTO (5% dry milk, 0.05 M Tris-HCl, pH 8.0, 0.15 M, NaCl) and incubated with a 1:500 dilution of sera in BLOTTO for one hour at 37° C. The presence of class 1 outer membrane proteins (OMPs) p1.5,2 and p1.7,16 is ascertained using monoclonal antibodies (supplied by J. T. Poolman). Reactive proteins are visualized with goat anti-mouse IgG and IgM conjugated to horseradish peroxidase (TAGO, Inc., Burlingame, Calif.), and development follows using 4-chloro-1-naphthol as the substrate.

Protein Quantitation

Total protein content is determined by Pierce's (Rockford, Ill.) BCA Protein Assay kit using bovine serum albumin as a standard.

Animal Studies

Each group of ten Swiss Webster mice, eight weeks old, are immunized subcutaneously with 25 $\mu$g of outer membranes, LOS-depleted outer membranes or LOS-depleted soluble outer membrane proteins in saline with 25 $\mu$g of 3-O-deacyl monophosphoryl lipid A (Ribi InmunoChem Research, Inc., Hamilton, Mont.) in a volume of 0.2 ml. Three vaccinations are administered at weeks zero, four, and eight. Mice are bled at the same intervals and exsanguinated at week ten. Pooled sera from each group are analyzed by immunoblot and enzyme-linked immunosorbent assay (ELISA). Immunoblotting is performed as described above and the sera tested at a 1:500 dilution against outer membrane complexes from H44/76 and 2996 cells and purified p1.7,16 outer membrane protein. ELISA assays utilize either whole cells of strains H44/76 or 2996 or purified class 1 omp. Bacteria are inactivated at 56° C. for one hour and diluted in sterile phosphate buffered saline (PBS: 27 mM KCl, 43 mM $NA_2HPO_4$.7 $H_2O$, 15 mM $KH_2PO_4$, 5 mM $MgCl_2$.6 $H_2O$, 1.4 M NaCl) to an $OD_{620}$ of 0.01–01. 96-well flat-bottomed microtiter plates (Nunc) are coated with 100 $\mu$l of cells and dried at 37° C. overnight in a dry incubator. Plates are washed three times with 0.05% TWEEN20™ in PBS (Wash Buffer). 0.3% TWEEN20™ and 10 mM EDTA in PBS are used to dilute the control and test sera, and 100 $\mu$l of these dilutions are added to the plates and incubated at room temperature for 60 minutes. Plates are again washed three times, 100 $\mu$l of 1:1000 dilution of goat anti-mouse IgG and IgM conjugated to alkaline phosphatase (TAGO) in 0.3% TWEEN20™$^{in\ PBS}$ are added, and the mixture is incubated at room temperature for one hour. Plates are washed three times, followed by a one hour incubation with 100 $\mu$l of the substrate nitrophenyl phosphate (Sigma) at 1.0 mg/ml in 1 M diethanolamine/0.5 mM magnesium chloride. The reaction is stopped by addition of 100 $\mu$l of 2 N NaOH, and the absorbance at 210 nm is read with 605 nm as a reference.

ELISA assays were also performed to detect antibodies to the class 1 outer membrane protein p1.7,16. 96-well flat-bottomed microtiter plates are coated with 100 $\mu$l of purified p1.7,16 at 5 $\mu$g/ml in 14 mM sodium carbonate/36 mM sodium bicarbonate, pH 9.6, 0.02% sodium azide buffer at 37° C. for 90 minutes. Plates are washed six times with PBS/0.1% TWEEN20™ (Wash Buffer). Serial dilutions of murine sera are made in PBS/0.05% TWEEN20™, 100 $\mu$il is added to each washed plate, and each plate is incubated for one hour at 37° C. Plates are again washed six times with Wash Buffer. 100 $\mu$l of a 1:2000 dilution of goat anti-mouse IgG and IgM conjugated to alkaline phosphatase are added, and the mixture is incubated for one hour at 37° C. Plates are washed as before, 100 $\mu$l of 1 mg/ml solution of nitrophenyl phosphate in diethanolamine are added, and the plates are allowed to incubate for one hour at room temperature. The reaction is stopped with 50 μl of 3 N sodium hydroxide, and the absorbance at 405 nm is read.

Bactericidal Assay

The assay procedure is modified from Høiby, E. A., et al., *NIPH Annals* 14(2):147–155 (1991). *N. meningitidis* strains are grown from frozen stock of GC agar media (Difco Laboratories, Detroit, Mich.) supplemented with dextrose (4 g/L), glutamine (0.1 g/L), cocarboxylase (0.2 mg/L), and ferric nitrate (5 mg/L). Plates are incubated for 6 hours at 35° C. in 5% $CO_2$. After growing for 6 hours, the colonies from one plate are used to inoculate 100 mL of liquid culture media consisting of 0.2% dialyzed yeast extract, L-glutamic acid (1.3 g/L), L-cysteine-HCl (0.02 g/L), sodium phosphate dihydrate, dibasic (10 g/L), potassium chloride (9.09 g/L), and ammonium chloride (1.25 g/L). This liquid culture is grown at 37° C. for 18 hours. An aliquot of the 18 hour culture is diluted to 20–30 Klett units or an optical density of 0.1 at 650 nm, and the culture is grown to late exponential phase. Once the cells reach late exponential phase, they are used in the bactericidal assay.

The bactericidal assay is carried out by mixing 10 μL *N. meningitidis* cells (about 2–4,000 bacteria), 10 μL complement (20% normal human sera), 25 μL PBS with 0.015 mM $CaCl_2$ and 0.5 mM $MgCl_2$ (PCM), and 5 μL diluted serum (PCM as diluent). The source of complement is pre-tested for lack of bactericidal activity by itself. The mix is incubated at 36° C. for 45 minutes, diluted at that time with 200 μL PCM, and 50 μL are plated onto GC agar plates. The culture plates are incubated for 24 hours at 35–36° C. with 5% $CO_2$. Colonies are then counted and bactericidal activity expressed as % control (no serum added). Titers are reported as the reciprocal of the dilution at which 50% of the bacteria in the assay are killed, as extrapolated from a plot of % killing vs. dilution. All sera are routinely tested at week 10. The highest concentration of sera tested is 1/50; any sera that do not kill at 1/50 are reported to have a titer of <50. Positive control antiserum, prepared against whole 2996 cells, is capable of utilizing the complement source to kill strain 2996 under these conditions.

Protection Studies

Groups of ten Swiss Webster mice, eight weeks old, were immunized subcutaneously with 25 μg of H44/76 LOS-depleted soluble outer membrane proteins, 2996 LOS-depleted soluble outer membrane proteins or both 25 μg of H44/76 LOS-depleted soluble outer membrane proteins and 25 μg of 2996 LOS-depleted soluble outer membrane proteins. The mixture of H44/76 LOS-depleted soluble outer membrane proteins and of 2996 LOS-depleted soluble outer membrane proteins was adjuvanted in QS-21 (Cambridge BioScience, Worcester, Mass.), and the H44/76 and 2996 LOS-depleted outer membrane proteins were adjuvanted in 3-O-deacyl monophosphoryl lipid A.

Vaccinations were administered at weeks zero and four. The mice were bled at the same intervals and exsanguinated at week 6. Pooled sera from each group were analyzed by immunoblot and ELISA.

Immunoblotting was performed as described above, and the sera tested at a 1:500 dilution against outer membrane complexes from H44/76 and 2996 cells. ELISA assays utilized whole cells of strains H44/76 or 2996. Bacteria are inactivated at 56° C. for one hour and diluted in sterile phosphate buffered saline (PBS: 27 mM KCl, 43 mM $NA_2HPO_4$.7 $H_2O$, 15 mM $KH_2PO_4$, 5 mM $MgCl_2$.6 $H_2O$, 1.4 M NaCl) to an $OD_{620}$ of 0.01–01. 96-well flat-bottomed microtiter plates (Nunc) are coated with 100 μl of cells and dried at 37° C. overnight in a dry incubator. 0.3% TWEEN20™ and 10 mM EDTA in PBS are used to dilute the control and test sera, and 100 μl of these dilutions are added to the plates and incubated at room temperature for 60 minutes. Plates are again washed three times, 100 μl of 1:1000 dilution of goat anti-mouse IgG, IgG1, IgG2a and IgG2b conjugated to alkaline phosphatase (TAGO) in 0.3% TWEEN20™$^{in\ PBS}$ is added, and the mixture is incubated at room temperature for one hour. Plates are washed three times, followed by a one hour incubation with 100 μl of the substrate nitrophenyl phosphate (Sigma) at 1.0 mg/ml in 1 M diethanolamine/0.5 mM magnesium chloride. The reaction is stopped by addition of 100 μl of 2 N NaOH, and the absorbance at 410 nm is read. Results are summarized in Table 6.

A bactericidal assay was also carried out as described above, utilizing H44/76 LOS-depleted soluble outer membrane proteins, 2996 LOS-depleted soluble outer membrane proteins or both of H44/76 LOS-depleted soluble outer membrane proteins and of 2996 LOS-depleted soluble outer membrane proteins. Results of this assay are summarized in Table 6.

Protective ability of the LOS-depleted soluble outer membrane proteins was tested using an infant rat challenge model as described in Saukkonen et al., *Microbial Pathogenesis* 3:261–267 (1987). Antisera generated from Swiss Webster mice as described above was administered to a group of five infant rats approximately four days old. After approximately twenty-four hours, the infant rats were challenged intraperitoneally with either H44/176 cells or 2996 cells. Approximately three hours after challenge, the number of colony forming units per ml of blood was determined.

TABLE 1

Endotoxin and Protein Content of Outer Membrane Preparations

| Preparation | Endotoxin (Eu) | Protein (Mg) |
|---|---|---|
| Outer Membranes | 22,360 | 448 |
| LOS-depleted Outer Membranes | 8 | 175 |
| LOS-depleted Soluble Outer Membrane Proteins | 7 | 30 |

Starting material for these preparations is 1.5 g dry weight of H13 cells.

Endotoxin units (Eu) are measured by turbidometric assay using *E. coli* lipopolysaccharide (LPS) as a standard, where 1 Eu=0.1 ng *E. coli* LPS.

TABLE 2

Endpoint Titers to Purified p1.7,16

| | Endpoint titers at weeks after primary immunization | | | |
|---|---|---|---|---|
| Immunogen | 0 | 4 | 8 | 10 |
| Outer Membranes | <100 | 6,287 | 63,946 | 142,416 |
| OM-LOS | <100 | 2,234 | 70,835 | 129,159 |
| SOMP-LOS | <100 | 20,355 | 192,939 | 199,068 |

OM-LOS, LOS-depleted outer membranes.
SOMP-LOS, LOS-depleted soluble outer membrane proteins.

TABLE 3

Endpoint ELISA Titers to H44/76 Whole Cells

| Immunogen | Endpoint titers at weeks after primary immunization | | | |
|---|---|---|---|---|
| | 0 | 4 | 8 | 10 |
| Outer Membranes | 248 | 21,726 | 122,674 | 388,553 |
| Zw3-12 OM-LOS | 0 | 30,345 | 297,971 | 90,546 |
| Zw3-14 OM-LOS | 6070 | 10,877 | 298,854 | 346,163 |
| SOMP-LOS | 0 | 30,728 | 270,977 | 320,328 |

Zw3-12 OM-LOS, LOS-depleted outer membranes prepared with Zw3-12.
Zw3-14 OM-LOS, LOS-depleted outer membranes prepared with Zw3-14.
SOMP-LOS, LOS-depleted soluble outer membrane proteins.

TABLE 4

Endpoint ELISA Titers to 2996 Whole Cells

| Immunogen | Endpoint titers at weeks after primary immunization | | | |
|---|---|---|---|---|
| | 0 | 4 | 8 | 10 |
| Outer Membranes | 0 | 7,120 | 71,166 | 137,506 |
| Zw3-12 OM-LOS | 0 | 9,437 | 130,823 | 79,852 |
| Zw3-14 OM-LOS | 0 | 6,970 | 231,942 | 118,969 |
| SOMP-LOS | 0 | 14,149 | 128,629 | 202,402 |

Zw3-12 OM-LOS, LOS-depleted outer membranes prepared with Zw3-12.
Zw3-14 OM-LOS, LOS-depleted outer membranes prepared with Zw3-14.
SOMP-LOS, LOS-depleted soluble outer membrane proteins.

TABLE 5

Bactericidal Activity of Antisera to LOS-Depleted Outer Membrane Preparations

| Immunogen | Bactericidal Titer of Strain | |
|---|---|---|
| | H44/76 | 2996 |
| Negative control (wk 0) | <50 | <50 |
| H13 Outer Membranes | 1,100 | <50 |
| H13 OM + partial LOS | 800 | <50 |
| H13 OM-LOS | 900 | <50 |
| H13 SOMP-LOS | 1,000 | <50 |
| 2996 Outer Membranes | <50 | 600 |
| 2996 OM-LOS | <50 | 225 |
| 2996 SOMP-LOS | <50 | 150 |

OM + partial LOS, outer membranes extracted once with Zw3-14 or twice with Zw3-12.
OM-LOS, LOS-depleted outer membranes.
SOMP-LOS, LOS-depleted soluble outer membrane proteins.
Titers are the reciprocal of the dilution that gave 50% killing.
The highest concentration of sera tested is 1/50; any sera that do not kill at 1/50 are reported to have a titer of <50.

TABLE 6

IMMUNOGENICITY OF SOLUBLE OUTER MEMBRANE PROTEINS

| | SAMPLE (ADJUVANT) | | |
|---|---|---|---|
| | H44/76 SOMPs (3DMPL) | 2996 SOMPs (3DMPL) | MIX (QS-21) |
| IGg WHOLE CELL ELISA TITER | | | |
| vs. H44/76 cells | $4.74 \times 10^5$ | $9.5 \times 10^4$ | $2.29 \times 10^6$ |
| vs. 2996 cells | $1.39 \times 10^4$ | $4.14 \times 10^4$ | $1.05 \times 10^6$ |

TABLE 6-continued

IMMUNOGENICITY OF SOLUBLE OUTER MEMBRANE PROTEINS

| | SAMPLE (ADJUVANT) | | |
|---|---|---|---|
| | H44/76 SOMPs (3DMPL) | 2996 SOMPs (3DMPL) | MIX (QS-21) |
| IgG1 WHOLE CELL ELISA TITER | | | |
| vs. H44/76 cells | $2.66 \times 10^4$ | $5.07 \times 10^3$ | $5.57 \times 10^4$ |
| vs. 2996 cells | $2.05 \times 10^3$ | $1.17 \times 10^4$ | $6.86 \times 10^3$ |
| IgG2a WHOLE CELL ELISA TITER | | | |
| vs. H44/76 cells | $3.92 \times 10^3$ | $2.14 \times 10^2$ | $2.07 \times 10^4$ |
| vs. 2996 cells | $1.71 \times 10^2$ | $9.73 \times 10^2$ | $4.52 \times 10^3$ |
| IgG2b WHOLE CELL ELISA TITER | | | |
| vs. H44/76 cells | $5.10 \times 10^3$ | $1.68 \times 10^2$ | $3.24 \times 10^3$ |
| vs. 2996 cells | <50 | $2.09 \times 10^3$ | $2.60 \times 10^3$ |
| BACTERICIDAL ANTIBODY TITER | | | |
| vs. H44/76 cells | 610 | <50 | >900 |
| vs. 2996 cells | <50 | 75 | 150 |

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. Isolated outer membranes containing less than about 0.01% by weight lipooligosaccharide, produced by a method comprising:

a) extracting total membranes of a Gram-negative coccus with a polyoxyethylene detergent to produce outer membranes depleted of inner membranes; and b) extracting the outer membranes produced by step a) with a zwitterionic betaine detergent to produce an insoluble fraction containing outer membranes containing less than about 0.01% by weight lipooligosaccharide and a soluble fraction containing lipooligosaccharide; and c) recovering the outer membranes from the insoluble fraction produced by step b).

2. Isolated outer membranes of claim 1, wherein the coccus is *Neisseria*.

3. Isolated outer membranes of claim 2, wherein the coccus is selected from the group consisting of *Neisseria meningitidis* and *Neisseria gonorrhoeae*.

4. Isolated outer membranes of claim 1, wherein the coccus is *Moraxella*.

5. Isolated outer membranes of claim 4, wherein the coccus is *Moraxella catarrhalis*.

6. Isolated outer membranes of claim 1, wherein the polyoxyethylene detergent is selected from the group consisting of:

a) nonaethylene glycol octylphenol ether;
   b) polyoxyethylene(23) lauryl ether; and
   c) polyoxyethylene sorbitan monooleate.

7. Isolated outer membranes of claim 1, wherein the zwitterionic betaine detergent has the formula:

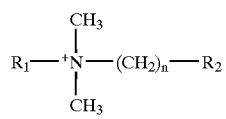

where R₁ is an alkyl chain with greater than 10 carbons and less than or equal to 16 carbons, R₂ is a carboxyl group or a sulfonyl group, and n is greater than 1.

8. Isolated outer membranes of claim 7, wherein the zwitterionic betaine detergent is selected from the group consisting of:
   a) R₂=a sulfonyl group, n=3 and R₁ is a C12 alkyl group;
   b) R₂=a sulfonyl group, n=3 and R₁ is a C14 alkyl group; and
   c) R₂=a carboxyl group, n=2 and R₁ is a C12 alkyl group.

9. Isolated outer membranes of claim 1, wherein step a) of the method is performed more than once before proceeding with step b).

10. Isolated outer membranes of claim 1, wherein step b) of the method is performed more than once.

11. Isolated soluble outer membrane proteins containing less than about 0.01% by weight lipooligosaccharide, produced by a method comprising:
   a) extracting total membranes of a Gram-negative coccus with a polyoxyethylene detergent to produce outer membranes depleted of inner membranes;
   b) extracting the outer membranes produced by step a) with a zwitterionic betaine detergent to produce an insoluble fraction containing outer membranes containing less than about 0.01% by weight lipooligosaccharide and a soluble fraction containing lipooligosaccharide;
   c) extracting the insoluble fraction containing outer membranes produced by step b) with a zwitterionic betaine detergent in salt buffer to produce a fraction containing soluble outer membrane proteins and a fraction containing insoluble outer membrane proteins and cell wall components; and
   d) isolating the soluble outer membrane proteins.

12. Isolated soluble outer membrane proteins of claim 11, wherein the coccus is *Neisseria*.

13. Isolated soluble outer membrane proteins of claim 12, wherein the coccus is selected from the group consisting of *Neisseria meningitidis* and *Neisseria gonorrhoeae*.

14. Isolated soluble outer membrane proteins of claim 11, wherein the coccus is *Moraxella*.

15. Isolated soluble outer membrane proteins of claim 14, wherein the coccus is *Moraxella catarrhalis*.

16. Isolated soluble outer membrane proteins of claim 11, wherein the polyoxyethylene detergent is selected from the group consisting of:
   a) nonaethylene glycol octylphenol ether;
   b) polyoxyethylene(23) lauryl ether; and
   c) polyoxyethylene sorbitan monooleate.

17. Isolated soluble outer membrane proteins of claim 11, wherein the zwitterionic betaine detergent has the formula:

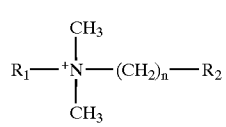

where R₁ is an alkyl chain with greater than 10 carbons and less than or equal to 16 carbons, R₂ is a carboxyl group or a sulfonyl group, and n is greater than 1.

18. Isolated soluble outer membrane proteins of claim 17, wherein the zwitterionic betaine detergent is selected from the group consisting of:
   a) R₂=a sulfonyl group, n=3 and R₁ is a C12 alkyl group;
   b) R₂=a sulfonyl group, n=3 and R₁ is a C14 alkyl group; and
   c) R₂=a carboxyl group, n=2 and R₁ is a C12 alkyl group.

19. Isolated soluble outer membrane proteins of claim 11, wherein the zwitterionic betaine detergent of step (c) has the following formula:

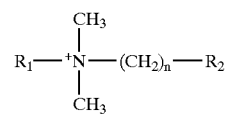

wherein R₂ is a sulfonyl group, n is 3 and R₁ is a C14 alkyl group, and
wherein the salt buffer is about 0.1 M to about 0.5 M NaCl.

20. Isolated soluble outer membrane proteins of claim 11, wherein the method further comprises concentrating the soluble outer membrane proteins.

21. Isolated insoluble outer membrane proteins and cell wall components containing less than about 0.01% by weight lipooligosaccharide, produced by a method comprising:
   a) extracting total membranes of a Gram-negative coccus with a polyoxyethylene detergent to produce outer membranes depleted of inner membranes;
   b) extracting the outer membranes produced by step a) with a zwitterionic betaine detergent to produce an insoluble fraction containing outer membranes containing less than about 0.01% by weight lipooligosaccharide and a soluble fraction containing lipooligosaccharide;
   c) extracting the insoluble fraction containing outer membranes produced by step b) with a zwitterionic betaine detergent in salt buffer to produce a fraction containing soluble outer membrane proteins and a fraction containing insoluble outer membrane proteins and cell wall components; and
   d) isolating the insoluble outer membrane proteins and cell wall components.

22. Isolated insoluble outer membrane proteins and cell wall components of claim 21, wherein the coccus is *Neisseria*.

23. Isolated insoluble outer membrane proteins and cell wall components of claim 22, wherein the coccus is selected from the group consisting of *Neisseria meningitidis* and *Neisseria gonorrhoeae*.

24. Isolated insoluble outer membrane proteins and cell wall components of claim 21, wherein the coccus is *Moraxella*.

25. Isolated insoluble outer membrane proteins and cell wall components of claim 24, wherein the coccus is *Moraxella catarrhalis*.

26. Isolated insoluble outer membrane proteins and cell wall components of claim 21, wherein the polyoxyethylene detergent is selected from the group consisting of:
   a) nonaethylene glycol octylphenol ether;
   b) polyoxyethylene(23) lauryl ether; and
   c) polyoxyethylene sorbitan monooleate.

27. Isolated insoluble outer membrane proteins and cell wall components of claim 21, wherein the zwitterionic betaine detergent has the formula:

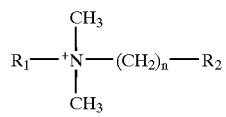

where $R_1$ is an alkyl chain with greater than 10 carbons and less than or equal to 16 carbons, $R_2$ is a carboxyl group or a sulfonyl group, and n is greater than 1.

28. Isolated insoluble outer membrane proteins and cell wall components of claim 27, wherein the zwitterionic betaine detergent is selected from the group consisting of:
 a) $R_2$=a sulfonyl group, n=3 and $R_1$ is a C12 alkyl group;
 b) $R_2$=a sulfonyl group, n=3 and $R_1$ is a C14 alkyl group; and
 c) $R_2$=a carboxyl group, n=2 and $R_1$ is a C12 alkyl group.

29. Isolated insoluble outer membrane proteins and cell wall components of claim 21, wherein the zwitterionic betaine detergent of step (c) has the following formula:

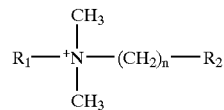

wherein $R_2$ is a sulfonyl group, n is 3 and $R_1$ is a C14 alkyl group, and wherein the salt buffer is about 0.1 M to about 0.5 M NaCl.

* * * * *